United States Patent [19]

Yanagita et al.

[11] Patent Number: 5,739,078
[45] Date of Patent: Apr. 14, 1998

[54] FLUORAN COMPOUNDS, INTERMEDIATES AND COLOR FORMING RECORDING MATERIALS

[75] Inventors: Mitsuhiro Yanagita; Takehiro Sato; Shigemi Suga; Tomoya Hidaka; Toru Kawabe, all of Ichihara; Mamoru Aizawa, Kyoto; Shinichi Sato; Izuo Aoki, both of Ichihara, all of Japan

[73] Assignee: Nippon Soda Co., Ltd., Tokyo, Japan

[21] Appl. No.: 663,135
[22] PCT Filed: Oct. 13, 1995
[86] PCT No.: PCT/JP95/02096
  § 371 Date: Aug. 22, 1996
  § 102(e) Date: Aug. 22, 1996
[87] PCT Pub. No.: WO96/11986
  PCT Pub. Date: Apr. 25, 1996

[30] Foreign Application Priority Data

Oct. 18, 1994 [JP] Japan ................. 6-278496
Feb. 14, 1995 [JP] Japan ................. 7-049172
Mar. 13, 1995 [JP] Japan ................. 7-080693

[51] Int. Cl.$^6$ .................................. C07D 493/10
[52] U.S. Cl. .................. 503/217; 503/220; 503/221; 503/223; 546/15; 548/407; 549/225
[58] Field of Search ............... 549/225; 548/407; 546/15; 503/217, 220, 221, 223

[56] References Cited

U.S. PATENT DOCUMENTS 4,954,631  9/1990  Obitsu et al. ................. 546/15

Primary Examiner—Richard L. Raymond
Attorney, Agent, or Firm—Jacobson, Price, Holman & Stern, PLLC

[57] ABSTRACT

By using the fluoran compound represented by the following general formula (I);

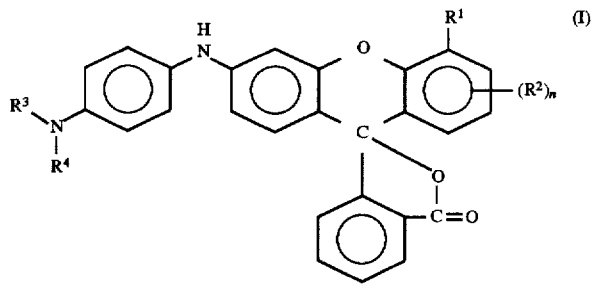

wherein $R^1$ is alkyl containing 1 to 4 carbon atoms, $R^3$ is alkyl containing 1 to 8 carbon atoms, $R^4$ is hydrogen or alkyl containing 1 to 8 carbon atoms, or $R^3$ and $R^4$ may bond with each other to form a ring together with a N atom, $R^2$ is alkyl containing 1 to 4 carbon atoms, and n denotes 0, 1 or 2, however, the substituents represented by $R^2$ may be different with each other when n is 2, as a color former for color forming recording materials, recording materials which have excellent properties in whiteness of the background of the material under light and in photostability of color-formed images on the materials as well as in sufficient color forming capability of the material even after having exposed them to light, can be provided.

4 Claims, No Drawings

FLUORAN COMPOUNDS, INTERMEDIATES AND COLOR FORMING RECORDING MATERIALS

This application is a 371 of PCT/JP95/02096, filed Oct. 13, 1995.

FIELD OF THE INVENTION

The present invention relates to fluoran compounds effectual as a color forming dyestuff to be used for color forming recording materials, such as thermal recording papers and pressure sensitive copying papers.

BACKGROUND ART

Today, the recording materials based on a color forming mechanism being composed of a reaction of a color former, which itself is colorless or with little color but forms color by reactions with a developer, and a developer to react with said color former to form color, have been widely used for pressure sensitive copying papers, thermal recording papers, etc. For such color forming dyestuffs, fluoran compounds have been mainly used, which can form various tones of color, such as black, green, red, blue, etc., respectively, depending upon the substituent contained in each of the fluoran compounds. Furthermore, some of the fluoran compounds can absorb even near infrared rays.

Recently, due to expanding use of thermal recording papers, opportunities to use thermal recording papers while exposing them to severe natural condition, has been increased. For this reason, an excellent property to preserve color-formed images on the papers and the background of the papers in good condition is requested for the fluoran compounds, however, there is no such compound capable of complying with such property. In case of thermal recording papers, therefore, the efficiency of the recording materials have been improved by using a composition added with a sensitizer for improving the sensitivity, an plasticity resistant agent for improving the preservability, an antioxidant, an ultraviolet rays absorbing agent, etc., other than the fluoran compound as the essential color former and the developer to react with the color former to form color. Furthermore, the means to improve the preservability of the papers by providing protective and intermediate layers to protect the color forming layer has been also carried out.

In Japanese Patent Laid-opened No. Sho 63-156790 Gazette, which has been filed by the applicant for the present invention, compounds having a chemical structure similar to the fluoran compounds of the present invention are disclosed, and the fluoran compounds of the present invention are contained in the scope of the claims of the said Gazette but are not specifically described therein.

For recording materials, particularly thermal and pressure sensitive recording papers, there is a problem in their photostability, namely the capability to preserve whiteness of the background of the papers after exposed them to light and the durability against discoloration of color-formed images thereon. In this respect, fluoran compounds previously known have disadvantages that those are unstable to light and decompose thereunder. Because of these disadvantageous properties, previous thermal recording papers tend to have problems that those do not form color even after giving heating or the density of color-formed images get very thin, when those have once been exposed to light. Therefore, it was obligatory to store such thermal recording papers in a dark place, since the color forming capability of such recording papers remarkably deteriorate in case those have once been exposed to light.

In the Japanese Patent Laid-opened No. Sho 63-156790 Gazette mentioned above, the recording material which has excellent photostability, particularly the one that does not result in discoloration of color-formed images on the materials due to light, is disclosed, however, there is no description therein on the color forming capability of the recording material after exposed it to light.

As described in the above, no fluoran compounds having satisfactory efficiency required for the color forming dyestuff has been found yet. Therefore, it is an object of the present invention to provide an recording material which has excellent properties in preservability to keep whiteness of the background of the recording material under light, in resistance to discoloration of color-formed images on the material due to light and in the sufficient color forming capability in the color-unformed part of the material even after exposed it to light.

DISCLOSURE OF THE INVENTION

The present invention is directed to fluoran compounds having at the 6-position an anilino group, wherein an p-substituted amino group is contained, and at the 4-position an alkyl group, represented by the following general formula (I):

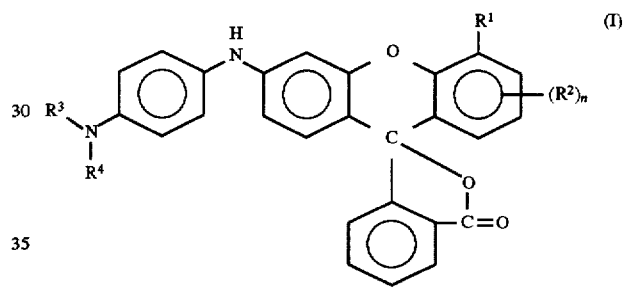

wherein $R^1$ is alkyl containing 1 to 4 carbon atoms, $R^3$ is alkyl containing 1 to 8 carbon atoms, $R^4$ is hydrogen or alkyl containing 1 to 8 carbon atoms, or $R^3$ and $R^4$ may bond to form a ring together with a N atom, $R^2$ is alkyl containing 1 to 4 carbon atoms, and n is 0, 1 or 2, however, the substituents represented by $R^2$ may be different with each other when n is 2, the intermediates thereof and color forming recording materials comprising said fluoran compound or the intermediate.

However, among the fluoran compounds represented by the general formula (I), it is more preferable to use the fluoran compounds represented by the following general formula (I');

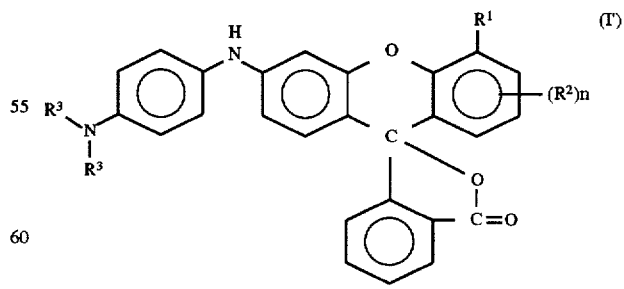

wherein $R^1$ is alkyl containing 1 to 4 carbon atoms, $R^3$ is alkyl containing 1 to 8 carbon atoms, $R^2$ is alkyl containing 1 to 4 carbon atoms, and n is 1 or 2, however, the substituents represented by $R^2$ may be different with each other when n is 2, as the color forming recording material.

For the concrete examples of the alkyl group containing 1 to 4 carbon atoms for the substituents, $R^1$ and $R^2$, in the compounds represented by the general formula (I), (I') and (II), methyl, ethyl, n-propyl, iso-propyl, n-butyl, iso-butyl, tert-butyl, etc. can be given.

Also, for the concrete examples of the alkyl group containing 1 to 8 carbon atoms for the substituents, $R^3$, $R^4$ and $R^5$, methyl, ethyl, n-propyl, iso-propyl, n-butyl, iso-butyl, tert-butyl, n-pentyl, iso-pentyl, neo-pentyl, tert-pentyl, n-hexyl, iso-hexyl, 1-methylpentyl, 2-methylpentyl, cyclohexyl, n-heptyl, n-octyl, etc. can be given.

When $R^3$ and $R^4$ bond to form a ring together with a N atom, a ring represented by a general formula, $-(CH_2)_m-$, wherein m is 4 or 5, can be given.

The fluoran compounds as represented by the general formula (I) can be manufactured according to the following reaction formula;

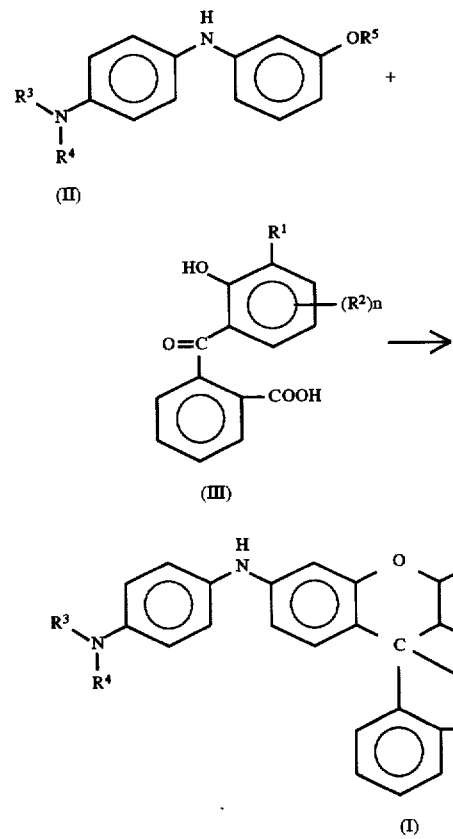

wherein $R^1$, $R^2$, $R^3$ and $R^4$ are as described above, and $R^5$ is hydrogen or alkyl containing 1 to 8 carbon atoms.

According to the reaction formula illustrated above, the fluoran compounds of the present invention can be prepared by condensing an aminophenol derivative represented by a general formula (II) and a benzoyl benzoic acid derivative represented by a general formula (III) for several to several dozens of hours in the presence of a dehydrating and condensing agent, such as sulfuric acid, phosphoric acid and acetic anhydride, and by subsequently subjecting the condensed product to intramolecular ring-closing reaction in an organic solvent in the presence of an alkaline substance. Namely, the fluoran compounds of the present invention can be prepared according to a manufacturing method generally known in the art for the fluoran compounds presently-used.

When the dehydrating and condensing agent used in the manufacturing of the fluoran compounds represented by the general formula (I) is sulfuric acid, the purity of the sulfuric acid is preferably more than 60%, and more preferably be in a range of from 80 to 100%. As the alternative dehydrating and condensing agents, fuming sulfuric acid, phosphoric acid anhydride, polyphosphoric acid, Lewis acid, such as phosphorus oxychloride and protonic acid, are exemplified, and those which can be used either by alone or by the combination of two or more of them. The combining rate of the diphenylamine derivative represented by the general formula (II) and the benzoyl benzoic acid derivative represented by the general formula (III) is preferably in a range of from 1:0.8 to 1:1.5, and more preferably from 1:1 to 1:1.2, in molar equivalent. The reaction temperature for the reaction is in a range of from $-20°$ to $80°$ C., and preferably from $-10°$ to $30°$ C.

The benzoyl benzoic acid derivative represented by the general formula (III) used in the present invention is generally prepared by reacting the corresponding phenol derivative with phthalic anhydride in an organic solvent in the presence of a catalyzer, Lewis acid or protonic acid. For the organic solvent, tetrachloroethane, chlorobenzene, dichlorobenzene (o-, m- and p-), etc. can be used as well as nitrobenzene and carbon disulfide. For the Lewis acid and the protonic acid, aluminium chloride, aluminium bromide, zinc chloride, iron(III) chloride, zirconium tetrachloride, thallium chloride, boron fluoride, tin(II) chloride, copper(II) chloride, sulfuric acid, phosphoric acid, etc. can be used. The rate of the catalyzer to 1 mol of the corresponding phenol derivative is in a range of from 2 to 15 molar equivalent, and more preferably from 2 to 4 molar equivalent. The reaction temperature is preferably in a range of from $-20°$ to $150°$ C., and more preferably from $20°$ to $120°$ C., and the reaction time is preferably in a range of from 2 to 72 hours.

Now, the concrete example for the manufacturing method for diphenylamine derivatives represented by the general formula (II) is described hereinbelow.

The manufacturing of the diphenylamine derivatives represented by the general formula (II), wherein if $R^5$ is hydrogen, and $R^3$ and $R^4$ are both methyl, can be attained according to the following reaction formula;

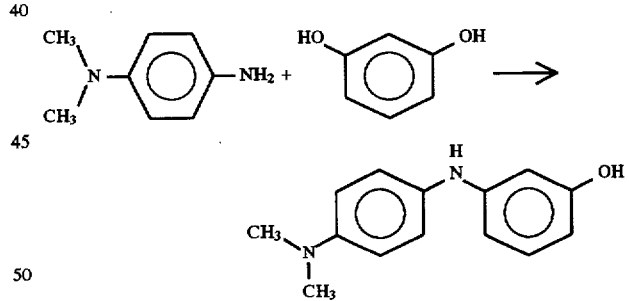

in an organic solvent and in the presence of a catalyzer, either Lewis acid or protonic acid.

For examples of the organic solvent used in the reaction said above, toluene, pseudocumene, xylene, chlorobenzene, dichlorobenzene (o-, m- and p-) can be given. As water results in during the reaction, it is preferable to distillate out the water from the reaction system by operating azeotropic distillation. For examples of the Lewis acid or the protonic acid to be used hereof, zinc chloride, calcium chloride, phosphoric acid, sulfuric acid, etc. can be given, and the reaction temperature shall preferably be maintained at a range of from $100°$ to $250°$ C., and more preferably from $150°$ to $210°$ C.

The manufacturing of the diphenylamine derivative represented by the general formula (II), wherein if all of $R^5$, $R^3$ and are methyl, can be attained according to the following reaction formula;

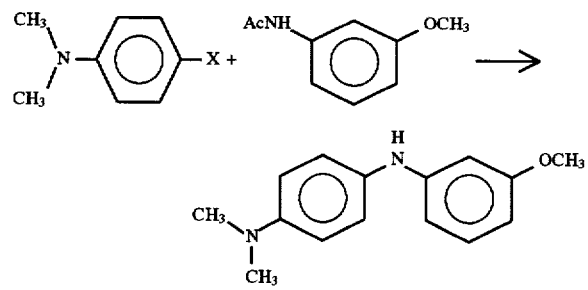

X=Br, I in an organic solvent and in the presence of catalytic copper, and further by subjecting the reacted product to the hydrolysis in the presence of either alkali or acid.

The organic solvent used in the reaction shown above, an aromatic solvent, such as toluene, pseudocumene and xylene, is preferably used, and again, it is preferable to distillate out water from the reaction system by operating azeotropic distillation, since water results in during the reaction as well. For the catalyzer used in the reaction, copper powder, copper(I) oxide, copper(II) oxide, copper(I) iodide, copper(II) nitrate, copper(II) hydroxide, copper(I) bromide, copper(II) bromide, copper(I) acetate, copper(II) acetate, copper(II) sulfate, tetraalkyl ammonium salts of tetrahalogenocopper(II), such as tetraethyl ammonium salt of tetrachlorocupric(II) acid, tetramethyl ammonium salt of tetrachlorocupric(II) acid, tetraethyl ammonium salt of tetrabromocupric(II) acid, tetramethyl ammonium salt of tetrabromocupric(II) acid and cetyltrimethyl ammonium salt of tetrachlorocupric(II) acid, bis(ethylenediamine) copper (II) dichloride, bis(N,N-diethylethylenediamine)copper(II) perchlorate, bis(2,2'-bipyridine)copper(II) dichloride hexahydrate, bis(2,2'-bipyridine)copper(II) diiodide, bis(2, 2'-bipyridine)copper(II) nitrate monohydrate, tris(2,2'-bipyridine)copper(II)nitrate hexahydrate, (2,2'-bipyridine) copper(II) nitrate trihydrate, (2,2'-bipyridine)copper(II) dibromide, (1,10-phenanthroline)copper(I) nitrate, chloro(1, 10-phenanthroline)(triphenylphosphin)copper(I), iodo(1,10-phenanthroline)(tri-n-butylphosphin)copper(I), bis(1,10-phenanthroline)copper(I) nitrate, bis(1,10-phenanthroline) copper(I) iodide, bis[iodo(1,10-phenanthroline)copper(I)], bis(1,10phenanthroline)copper(II) dichloride, tris(1,10-phenanthroline)copper(II) nitrate, bis(4,7-diphenyl-1,10-phenanthroline)copper(II) dichloride, (1,10-phenanthroline) copper(II) nitrate, bis(1,10-phenanthroline)copper(II) nitrate, (1,10-phenanthroline)copper(II) dibromide, bis(1, 10-phenanthroline)copper(II) nitrate, (1,10-phenanthroline) copper(II) sulfate, bis(dimethylgtyoximato)copper(II), dichloro(dimethylglyoxime)copper(II), potassium bis (glycylglycinato)cuprate(II) hexahydrate, chloro (glycylglycinato)aquacopper(II), bis(glycinato)copper(II) monohydrate, bis(alaninato)copper(II), bis (salicylaldehydeoximato)copper(II), bis(2-aminoethanolato) copper monohydrate, bis(8-quinolirato)copper(II), etc. can be given. In addition, sodium carbonate and potassium carbonate can be used as a neutralizing agent. The temperature required for the reaction is in a range of from 120° to 250° C., and more preferably from 170° to 220° C. Moreover, ordinary acid or alkali, such as sulfuric acid, hydrochloric acid, sodium hydroxide and potassium hydroxide, can be used to take place the hydrolysis.

Now, the representative examples for the fluoran compounds of the present invention represented by the general formula (I) are given in Table 1 hereinbelow.

TABLE 1

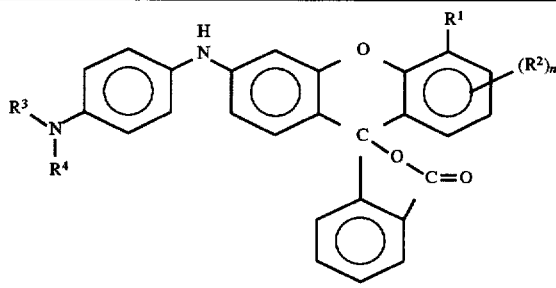

| Compound No. | R¹ | R² (n = 1) | R² (n = 2) | R³ | R⁴ | Melting Point °C. |
|---|---|---|---|---|---|---|
| (1) | Me | 2-Me | — | Me | Me | 234.5–234.7 |
| (2) | Me | 3-Me | — | Me | Me | 215.7–216.6 |
| (3) | Me | 1-Me | — | Me | Me | — |
| (4) | Me | 1-Me | 3-Me | Me | Me | 244.2–245.5 |
| (5) | Me | 1-Me | 2-Me | Me | Me | — |
| (6) | Et | 2-Et | — | Me | Me | — |
| (7) | Et | 3-Et | — | Me | Me | — |
| (8) | Et | 1-Et | — | Me | Me | — |
| (9) | Et | 1-Et | 3-Et | Me | Me | — |
| (10) | Et | 1-Et | 2-Et | Me | Me | — |
| (11) | iso-Pr | 2-iso-Pr | — | Me | Me | — |
| (12) | iso-Pr | 3-iso-Pr | — | Me | Me | — |
| (13) | iso-Pr | 1-iso-Pr | — | Me | Me | — |
| (14) | iso-Pr | 1-iso-Pr | 3-iso-Pr | Me | Me | — |
| (15) | iso-Pr | 1-iso-Pr | 2-iso-Pr | Me | Me | — |
| (16) | iso-Bu | 2-iso-Bu | — | Me | Me | — |
| (17) | iso-Bu | 3-iso-Bu | — | Me | Me | — |
| (18) | iso-Bu | 1-iso-Bu | — | Me | Me | — |

TABLE 1-continued

| Compound No. | R¹ | R² (n = 1) | R² (n = 2) | R³ | R⁴ | Melting Point °C. |
|---|---|---|---|---|---|---|
| (19) | iso-Bu | 1-iso-Bu | 3-iso-Bu | Me | Me | — |
| (20) | iso-Bu | 1-iso-Bu | 2-iso-Bu | Me | Me | — |
| (21) | tert-Bu | 2-tert-Bu | — | Me | Me | 218.6–221.5 |
| (22) | tert-Bu | 3-tert-Bu | — | Me | Me | — |
| (23) | tert-Bu | 1-tert-Bu | — | Me | Me | — |
| (24) | tert-Bu | 1-tert-Bu | 3-tert-Bu | Me | Me | — |
| (25) | tert-Bu | 1-tert-Bu | 2-tert-Bu | Me | Me | — |
| (26) | Et | 2-Me | — | Me | Me | — |
| (27) | iso-Pr | 2-Me | — | Me | Me | — |
| (28) | n-Bu | 2-Me | — | Me | Me | — |
| (29) | tert-Bu | 2-Me | — | Me | Me | 215.8–230.6 |
| (30) | Me | 2-n-Pr | — | Me | Me | — |
| (31) | Me | 2-n-Bu | — | Me | Me | — |
| (32) | Me | 2-tert-Bu | — | Me | Me | — |
| (33) | Me | — | — | Me | Me | — |
| (34) | Me | 2-Me | — | Et | Et | 200.4–201.2 |
| (35) | Me | 3-Me | — | Et | Et | — |
| (36) | Me | 1-Me | — | Et | Et | — |
| (37) | Me | 1-Me | 3-Me | Et | Et | — |
| (38) | Me | 1-Me | 2-Me | Et | Et | — |
| (39) | Et | 2-Et | — | Et | Et | — |
| (40) | Et | 3-Et | — | Et | Et | — |
| (41) | Et | 1-Et | — | Et | Et | — |
| (42) | Et | 1-Et | 3-Et | Et | Et | — |
| (43) | Et | 1-Et | 2-Et | Et | Et | — |
| (44) | iso-Pr | 2-iso-Pr | — | Et | Et | — |
| (45) | iso-Pr | 3-iso-Pr | Et | Et | — | — |
| (46) | iso-Pr | 1-iso-Pr | — | Et | Et | — |
| (47) | iso-Pr | 1-iso-Pr | 3-iso-Pr | Et | Et | — |
| (48) | iso-Pr | 1-iso-Pr | 2-iso-Pr | Et | Et | — |
| (49) | iso-Bu | 2-iso-Bu | — | Et | Et | — |
| (50) | iso-Bu | 3-iso-Bu | — | Et | Et | — |
| (51) | iso-Bu | 1-iso-Bu | — | Et | Et | — |
| (52) | iso-Bu | 1-iso-Bu | 3-iso-Bu | Et | Et | — |
| (53) | iso-Bu | 1-iso-Bu | 2-iso-Bu | Et | Et | — |
| (54) | tert-Bu | 2-tert-Bu | — | Et | Et | — |
| (55) | tert-Bu | 3-tert-Bu | — | Et | Et | — |
| (56) | tert-Bu | 1-tert-Bu | — | Et | Et | — |
| (57) | tert-Bu | 1-tert-Bu | 3-tert-Bu | Et | Et | — |
| (58) | tert-Bu | 1-tert-Bu | 2-tert-Bu | Et | Et | — |
| (59) | Et | 2-Me | — | Et | Et | — |
| (60) | iso-Pr | 2-Me | — | Et | Et | — |
| (61) | n-Bu | 2-Me | — | Et | Et | — |
| (62) | tert-Bu | 2-Me | — | Et | Et | — |
| (63) | Me | 2-n-Pr | — | Et | Et | — |
| (64) | Me | 2-n-Bu | — | Et | Et | — |
| (65) | Me | 2-tert-Bu | — | Et | Et | — |
| (66) | Me | — | — | Et | Et | — |
| (67) | Me | 2-Me | — | n-Pr | n-Pr | 190.1–190.6 |
| (68) | Me | 3-Me | — | n-Pr | n-Pr | — |
| (69) | Me | 1-Me | — | n-Pr | n-Pr | — |
| (70) | Me | 1-Me | 3-Me | n-Pr | n-Pr | — |
| (71) | Me | 1-Me | 2-Me | n-Pr | n-Pr | — |
| (72) | Et | 2-Et | — | n-Pr | n-Pr | — |
| (73) | Et | 3-Et | — | n-Pr | n-Pr | — |
| (74) | Et | 1-Et | — | n-Pr | n-Pr | — |
| (75) | Et | 1-Et | 3-Et | n-Pr | n-Pr | — |
| (76) | Et | 1-Et | 2-Et | n-Pr | n-Pr | — |
| (77) | iso-Pr | 2-iso-Pr | — | n-Pr | n-Pr | — |
| (78) | iso-Pr | 3-iso-Pr | — | n-Pr | n-Pr | — |
| (79) | iso-Pr | 1-iso-Pr | — | n-Pr | n-Pr | — |
| (80) | iso-Pr | 1-iso-Pr | 3-iso-Pr | n-Pr | n-Pr | — |

TABLE 1-continued

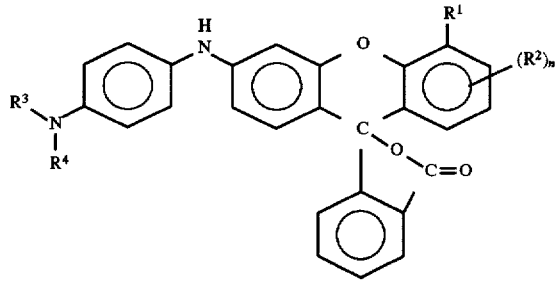

| Compound No. | R¹ | R² (n = 1) | R² (n = 2) | R³ | R⁴ | Melting Point °C. |
|---|---|---|---|---|---|---|
| (81) | iso-Pr | 1-iso-Pr | 2-iso-Pr | n-Pr | n-Pr | — |
| (82) | iso-Bu | 2-iso-Bu | — | n-Pr | n-Pr | — |
| (83) | iso-Bu | 3-iso-Bu | — | n-Pr | n-Pr | — |
| (84) | iso-Bu | 1-iso-Bu | — | n-Pr | n-Pr | — |
| (85) | iso-Bu | 1-iso-Bu | 3-iso-Bu | n-Pr | n-Pr | — |
| (86) | iso-Bu | 1-iso-Bu | 2-iso-Bu | n-Pr | n-Pr | — |
| (87) | tert-Bu | 2-tert-Bu | — | n-Pr | n-Pr | — |
| (88) | tert-Bu | 3-tert-Bu | — | n-Pr | n-Pr | — |
| (89) | tert-Bu | 1-tert-Bu | — | n-Pr | n-Pr | — |
| (90) | tert-Bu | 1-tert-Bu | 3-tert-Bu | n-Pr | n-Pr | — |
| (91) | tert-Bu | 1-tert-Bu | 2-tert-Bu | n-Pr | n-Pr | — |
| (92) | Et | 2-Me | — | n-Pr | n-Pr | — |
| (93) | iso-Pr | 2-Me | — | n-Pr | n-Pr | — |
| (94) | n-Bu | 2-Me | — | n-Pr | n-Pr | — |
| (95) | tert-Bu | 2-Me | — | n-Pr | n-Pr | — |
| (96) | Me | 2-n-Pr | — | n-Pr | n-Pr | — |
| (97) | Me | 2-n-Bu | — | n-Pr | n-Pr | — |
| (98) | Me | 2-tert-Bu | — | n-Pr | n-Pr | — |
| (99) | Me | — | — | n-Pr | n-Pr | — |
| (100) | Me | 2-Me | — | n-Bu | n-Bu | 193.0–193.8 |
| (101) | Me | 3-Me | — | n-Bu | n-Bu | — |
| (102) | Me | 1-Me | — | n-Bu | n-Bu | — |
| (103) | Me | 1-Me | 3-Me | n-Bu | n-Bu | 192.1–192.6 |
| (104) | Me | 1-Me | 2-Me | n-Bu | n-Bu | — |
| (105) | Et | 2-Et | — | n-Bu | n-Bu | — |
| (106) | Et | 3-Et | — | n-Bu | n-Bu | — |
| (107) | Et | 1-Et | — | n-Bu | n-Bu | — |
| (108) | Et | 1-Et | 3-Et | n-Bu | n-Bu | — |
| (109) | Et | 1-Et | 2-Et | n-Bu | n-Bu | — |
| (110) | iso-Pr | 2-iso-Pr | — | n-Bu | n-Bu | — |
| (111) | iso-Pr | 3-iso-Pr | — | n-Bu | n-Bu | — |
| (112) | iso-Pr | 1-iso-Pr | — | n-Bu | n-Bu | — |
| (113) | iso-Pr | 1-iso-Pr | 3-iso-Pr | n-Bu | n-Bu | — |
| (114) | iso-Pr | 1-iso-Pr | 2-iso-Pr | n-Bu | n-Bu | — |
| (115) | iso-Bu | 2-iso-Bu | — | n-Bu | n-Bu | — |
| (116) | iso-Bu | 3-iso-Bu | — | n-Bu | n-Bu | — |
| (117) | iso-Bu | 1-iso-Bu | — | n-Bu | n-Bu | — |
| (118) | iso-Bu | 1-iso-Bu | 3-iso-Bu | n-Bu | n-Bu | — |
| (119) | iso-Bu | 1-iso-Bu | 2-iso-Bu | n-Bu | n-Bu | — |
| (120) | tert-Bu | 2-tert-Bu | — | n-Bu | n-Bu | — |
| (121) | tert-Bu | 3-tert-Bu | — | n-Bu | n-Bu | — |
| (122) | tert-Bu | 1-tert-Bu | — | n-Bu | n-Bu | — |
| (123) | tert-Bu | 1-tert-Bu | 3-tert-Bu | n-Bu | n-Bu | — |
| (124) | tert-Bu | 1-tert-Bu | 2-tert-Bu | n-Bu | n-Bu | — |
| (125) | Et | 2-Me | — | n-Bu | n-Bu | — |
| (126) | iso-Pr | 2-Me | — | n-Bu | n-Bu | — |
| (127) | n-Bu | 2-Me | — | n-Bu | n-Bu | — |
| (128) | tert-Bu | 2-Me | — | n-Bu | n-Bu | — |
| (129) | Me | 2-n-Pr | — | n-Bu | n-Bu | — |
| (130) | Me | 2-n-Bu | — | n-Bu | n-Bu | — |
| (131) | Me | 2-tert-Bu | — | n-Bu | n-Bu | — |
| (132) | Me | — | — | n-Bu | n-Bu | — |
| (133) | Me | 2-Me | — | n-Pen | n-Pen | — |
| (134) | Me | 1-Me | 3-Me | n-Pen | n-Pen | — |
| (135) | tert-Bu | 2-tert-Bu | — | n-Pen | n-Pen | — |
| (136) | tert-Bu | 2-Me | — | n-Pen | n-Pen | — |
| (137) | Me | 2-Me | — | n-Hex | n-Hex | 145.0–147.0 |
| (138) | Me | 1-Me | 3-Me | n-Hex | n-Hex | — |
| (139) | tert-Bu | 2-tert-Bu | — | n-Hex | n-Hex | — |
| (140) | tert-Bu | 2-Me | — | n-Hex | n-Hex | — |
| (141) | Me | 2-Me | — | n-Hep | n-Hep | — |
| (142) | Me | 1-Me | 3-Me | n-Hep | n-Hep | — |

TABLE 1-continued

| Compound No. | R¹ | R² (n = 1) | R² (n = 2) | R³ | R⁴ | Melting Point °C. |
|---|---|---|---|---|---|---|
| (143) | tert-Bu | 2-tert-Bu | — | n-Hep | n-Hep | — |
| (144) | tert-Bu | 2-Me | — | n-Hep | n-Hep | — |
| (145) | Me | 2-Me | — | n-Oct | n-Oct | — |
| (146) | Me | 1-Me | 3-Me | n-Oct | n-Oct | — |
| (147) | tert-Bu | 2-tert-Bu | — | n-Oct | n-Oct | — |
| (148) | tert-Bu | 2-Me | — | n-Oct | n-Oct | — |
| (149) | Me | 2-Me | — | —CH₂CH₂CH₂CH₂— | | — |
| (150) | Me | 1-Me | 3-Me | —CH₂CH₂CH₂CH₂— | | — |
| (151) | tert-Bu | 2-tert-Bu | — | —CH₂CH₂CH₂CH₂— | | — |
| (152) | tert-Bu | 2-Me | — | —CH₂CH₂CH₂CH₂— | | — |
| (153) | Me | 2-Me | — | —CH₂CH₂CH₂CH₂CH₂— | | — |
| (154) | Me | 1-Me | 3-Me | —CH₂CH₂CH₂CH₂CH₂— | | — |
| (155) | tert-Bu | 2-tert-Bu | — | —CH₂CH₂CH₂CH₂CH₂— | | — |
| (156) | tert-Bu | 2-Me | — | —CH₂CH₂CH₂CH₂CH₂— | | — |
| (157) | Me | 2-Me | — | Me | Et | — |
| (158) | Me | 1-Me | 3-Me | Me | Et | — |
| (159) | tert-Bu | 2-tert-Bu | — | Me | Et | — |
| (160) | tert-Bu | 2-Me | — | Me | Et | — |
| (161) | Me | 2-Me | — | Me | n-Pr | — |
| (162) | Me | 1-Me | 3-Me | Me | n-Pr | — |
| (163) | tert-Bu | 2-tert-Bu | — | Me | n-Pr | — |
| (164) | tert-Bu | 2-Me | — | Me | n-Pr | — |
| (165) | Me | 2-Me | — | Me | n-Bu | — |
| (166) | Me | 1-Me | 3-Me | Me | n-Bu | — |
| (167) | tert-Bu | 2-tert-Bu | — | Me | n-Bu | — |
| (168) | tert-Bu | 2-Me | — | Me | n-Bu | — |
| (169) | Me | 2-Me | — | Me | n-Hex | — |
| (170) | Me | 1-Me | 3-Me | Me | n-Hex | — |
| (171) | tert-Bu | 2-tert-Bu | — | Me | n-Hex | — |
| (172) | tert-Bu | 2-Me | — | Me | n-Hex | — |
| (173) | Me | 2-Me | — | Me | n-Oct | — |
| (174) | Me | 1-Me | 3-Me | Me | n-Oct | — |
| (175) | tert-Bu | 2-tert-Bu | — | Me | n-Oct | — |
| (176) | tert-Bu | 2-Me | — | Me | n-Oct | — |
| (177) | Me | 2-Me | — | Et | n-Pr | — |
| (178) | Me | 1-Me | 3-Me | Et | n-Pr | — |
| (179) | tert-Bu | 2-tert-Bu | — | Et | n-Pr | — |
| (180) | tert-Bu | 2-Me | — | Et | n-Pr | — |
| (181) | Me | 2-Me | — | Et | n-Bu | — |
| (182) | Me | 1-Me | 3-Me | Et | n-Bu | — |
| (183) | tert-Bu | 2-tert-Bu | — | Et | n-Bu | — |
| (184) | tert-Bu | 2-Me | — | Et | n-Bu | — |
| (185) | Me | 2-Me | — | Et | n-Hex | — |
| (186) | Me | 1-Me | 3-Me | Et | n-Hex | — |
| (187) | tert-Bu | 2-tert-Bu | — | Et | n-Hex | — |
| (188) | tert-Bu | 2-Me | — | Et | n-Hex | — |
| (189) | Me | 2-Me | — | Et | n-Oct | — |
| (190) | Me | 1-Me | 3-Me | Et | n-Oct | — |
| (191) | tert-Bu | 2-tert-Bu | — | Et | n-Oct | — |
| (192) | tert-Bu | 2-Me | — | Et | n-Oct | — |
| (193) | Me | 2-Me | — | n-Pr | n-Bu | — |
| (194) | Me | 1-Me | 3-Me | n-Pr | n-Bu | — |
| (195) | tert-Bu | 2-tert-Bu | — | n-Pr | n-Bu | — |
| (196) | tert-Bu | 2-Me | — | n-Pr | n-Bu | — |
| (197) | Me | 2-Me | — | n-Pr | n-Hex | — |
| (198) | Me | 1-Me | 3-Me | n-Pr | n-Hex | — |
| (199) | tert-Bu | 2-tert-Bu | — | n-Pr | n-Hex | — |
| (200) | tert-Bu | 2-Me | — | n-Pr | n-Hex | — |
| (201) | Me | 2-Me | — | n-Pr | n-Oct | — |
| (202) | Me | 1-Me | 3-Me | n-Pr | n-Oct | — |
| (203) | tert-Bu | 2-tert-Bu | — | n-Pr | n-Oct | — |
| (204) | tert-Bu | 2-Me | — | n-Pr | n-Oct | — |

TABLE 1-continued

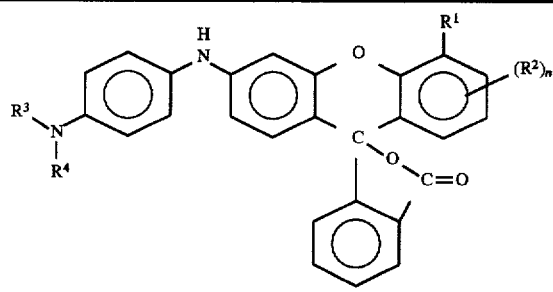

| Compound No. | R¹ | R² (n = 1) | R² (n = 2) | R³ | R⁴ | Melting Point °C. |
|---|---|---|---|---|---|---|
| (205) | Me | 2-Me | — | n-Bu | n-Hex | — |
| (206) | Me | 1-Me | 3-Me | n-Bu | n-Hex | — |
| (207) | tert-Bu | 2-tert-Bu | — | n-Bu | n-Hex | — |
| (208) | tert-Bu | 2-Me | — | n-Bu | n-Hex | — |
| (209) | Me | 2-Me | — | n-Bu | n-Oct | — |
| (210) | Me | 1-Me | 3-Me | n-Bu | n-Oct | — |
| (211) | tert-Bu | 2-tert-Bu | — | n-Bu | n-Oct | — |
| (212) | tert-Bu | 2-Me | — | n-Bu | n-Oct | — |
| (213) | Me | 2-Me | — | n-Hex | n-Oct | — |
| (214) | Me | 1-Me | 3-Me | n-Hex | n-Oct | — |
| (215) | tert-Bu | 2-tert-Bu | — | n-Hex | n-Oct | — |
| (216) | tert-Bu | 2-Me | — | n-Hex | n-Oct | — |
| (217) | Me | 2-Me | — | Me | H | — |
| (218) | Me | 1-Me | 3-Me | Me | H | — |
| (219) | tert-Bu | 2-tert-Bu | — | Me | H | — |
| (220) | tert-Bu | 2-Me | — | Me | H | — |
| (221) | Me | 2-Me | — | Et | H | — |
| (222) | Me | 1-Me | 3-Me | Et | H | — |
| (223) | tert-Bu | 2-tert-Bu | — | Et | H | — |
| (224) | tert-Bu | 2-Me | — | Et | H | — |
| (225) | Me | 2-Me | — | n-Pr | H | — |
| (226) | Me | 1-Me | 3-Me | n-Pr | H | — |
| (227) | tert-Bu | 2-tert-Bu | — | n-Pr | H | — |
| (228) | tert-Bu | 2-Me | — | n-Pr | H | — |
| (229) | Me | 2-Me | — | n-Bu | H | — |
| (230) | Me | 1-Me | 3-Me | n-Bu | H | — |
| (231) | tert-Bu | 2-tert-Bu | — | n-Bu | H | — |
| (232) | tert-Bu | 2-Me | — | n-Bu | H | — |
| (233) | Me | 2-Me | — | n-Hex | H | — |
| (234) | Me | 1-Me | 3-Me | n-Hex | H | — |
| (235) | tert-Bu | 2-tert-Bu | — | n-Hex | H | — |
| (236) | tert-Bu | 2-Me | — | n-Hex | H | — |
| (237) | Me | 2-Me | — | n-Oct | H | — |
| (238) | Me | 1-Me | 3-Me | n-Oct | H | — |
| (239) | tert-Bu | 2-tert-Bu | — | n-Oct | H | — |
| (240) | tert-Bu | 2-Me | — | n-Oct | H | — |
| (241) | Me | 2-Me | — | iso-Pr | H | — |
| (242) | Me | 1-Me | 3-Me | iso-Pr | H | — |
| (243) | tert-Bu | 2-tert-Bu | — | iso-Pr | H | — |
| (244) | tert-Bu | 2-Me | — | iso-Pr | H | — |
| (245) | Me | 2-Me | — | iso-Bu | H | — |
| (246) | Me | 1-Me | 3-Me | iso-Bu | H | — |
| (247) | tert-Bu | 2-tert-Bu | — | iso-Bu | H | — |
| (248) | tert-Bu | 2-Me | — | iso-Bu | H | — |
| (249) | Me | 2-Me | — | sec-Bu | H | — |
| (250) | Me | 1-Me | 3-Me | sec-Bu | H | — |
| (251) | tert-Bu | 2-tert-Bu | — | sec-Bu | H | — |
| (252) | tert-Bu | 2-Me | — | sec-Bu | H | — |
| (253) | Me | 2-Me | — | iso-Pro | iso-Pro | — |
| (254) | Me | 1-Me | 3-Me | iso-Pro | iso-Pro | — |
| (255) | tert-Bu | 2-tert-Bu | — | iso-Pro | iso-Pro | — |
| (256) | tert-Bu | 2-Me | — | iso-Pro | iso-Pro | — |
| (257) | Me | 2-Me | — | iso-Bu | iso-Bu | — |
| (258) | Me | 1-Me | 3-Me | iso-Bu | iso-Bu | — |
| (259) | tert-Bu | 2-tert-Bu | — | iso-Bu | iso-Bu | — |
| (260) | tert-Bu | 2-Me | — | iso-Bu | iso-Bu | — |
| (261) | Me | 2-Me | — | sec-Bu | sec-Bu | — |
| (262) | Me | 1-Me | 3-Me | sec-Bu | sec-Bu | — |
| (263) | tert-Bu | 2-tert-Bu | — | sec-Bu | sec-Bu | — |
| (264) | tert-Bu | 2-Me | — | sec-Bu | sec-Bu | — |
| (265) | Me | 2-Me | — | tert-Bu | tert-Bu | — |
| (266) | Me | 1-Me | 3-Me | tert-Bu | tert-Bu | — |

TABLE 1-continued

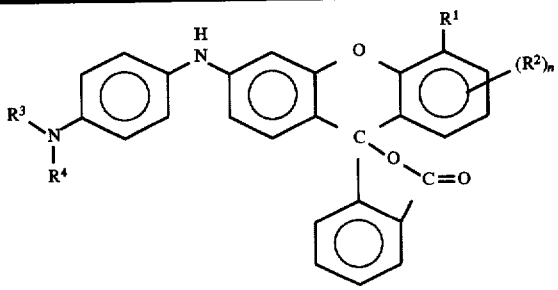

| Compound No. | R¹ | R² (n = 1) | R² (n = 2) | R³ | R⁴ | Melting Point °C. |
|---|---|---|---|---|---|---|
| (267) | tert-Bu | 2-tert-Bu | — | tert-Bu | tert-Bu | — |
| (268) | tert-Bu | 2-Me | — | tert-Bu | tert-Bu | — |
| (269) | Me | 2-Me | — | cyclo-Hex | H | — |
| (270) | Me | 1-Me | 3-Me | cyclo-Hex | H | — |
| (271) | tert-Bu | 2-tert-Bu | — | cyclo-Hex | H | — |
| (272) | tert-Bu | 2-Me | — | cyclo-Hex | H | — |
| (273) | Me | 2-Me | — | cyclo-Hex | Me | — |
| (274) | Me | 1-Me | 3-Me | cyclo-Hex | Me | — |
| (275) | tert-Bu | 2-tert-Bu | — | cyclo-Hex | Me | — |
| (276) | tert-Bu | 2-Me | — | cyclo-Hex | Me | — |
| (277) | Me | 2-Me | — | cyclo-Hex | Et | — |
| (278) | Me | 1-Me | 3-Me | cyclo-Hex | Et | — |
| (279) | tert-Bu | 2-tert-Bu | — | cyclo-Hex | Et | — |
| (280) | tert-Bu | 2-Me | — | cyclo-Hex | Et | — |
| (281) | Me | 2-Me | — | cyclo-Hex | n-Pr | — |
| (282) | Me | 1-Me | 3-Me | cyclo-Hex | n-Pr | — |
| (283) | tert-Bu | 2-tert-Bu | — | cyclo-Hex | n-Pr | — |
| (284) | tert-Bu | 2-Me | — | cyclo-Hex | n-Pr | — |
| (285) | Me | 2-Me | — | cyclo-Hex | iso-Pr | — |
| (286) | Me | 1-Me | 3-Me | cyclo-Hex | iso-Pr | — |
| (287) | tert-Bu | 2-tert-Bu | — | cyclo-Hex | iso-Pr | — |
| (288) | tert-Bu | 2-Me | — | cyclo-Hex | iso-Pr | — |
| (289) | Me | 2-Me | — | cyclo-Hex | iso-Bu | — |
| (290) | Me | 1-Me | 3-Me | cyclo-Hex | iso-Bu | — |
| (291) | tert-Bu | 2-tert-Bu | — | cyclo-Hex | iso-Bu | — |
| (292) | tert-Bu | 2-Me | — | cyclo-Hex | iso-Bu | — |
| (293) | Me | 2-Me | — | cyclo-Hex | tert-Bu | — |
| (294) | Me | 1-Me | 3-Me | cyclo-Hex | tert-Bu | — |
| (295) | tert-Bu | 2-tert-Bu | — | cyclo-Hex | tert-Bu | — |
| (296) | tert-Bu | 2-Me | — | cyclo-Hex | tert-Bu | — |
| (297) | Me | 2-Me | — | cyclo-Hex | n-Hex | — |
| (298) | Me | 1-Me | 3-Me | cyclo-Hex | n-Hex | — |
| (299) | tert-Bu | 2-tert-Bu | — | cyclo-Hex | n-Hex | — |
| (300) | tert-Bu | 2-Me | — | cyclo-Hex | n-Hex | — |
| (301) | Me | 2-Me | — | cyclo-Hex | n-Oct | — |
| (302) | Me | 1-Me | 3-Me | cyclo-Hex | n-Oct | — |
| (303) | tert-Bu | 2-tert-Bu | — | cyclo-Hex | n-Oct | — |
| (304) | tert-Bu | 2-Me | — | cyclo-Hex | n-Oct | — |
| (305) | Me | 2-Me | — | iso-Pr | Me | — |
| (306) | Me | 1-Me | 3-Me | iso-Pr | Me | — |
| (307) | tert-Bu | 2-tert-Bu | — | iso-Pr | Me | — |
| (308) | tert-Bu | 2-Me | — | iso-Pr | Me | — |
| (309) | Me | 2-Me | — | iso-Pr | Et | — |
| (310) | Me | 1-Me | 3-Me | iso-Pr | Et | — |
| (311) | tert-Bu | 2-tert-Bu | — | iso-Pr | Et | — |
| (312) | tert-Bu | 2-Me | — | iso-Pr | Et | — |
| (313) | Me | 2-Me | — | iso-Pr | n-Pr | — |
| (314) | Me | 1-Me | 3-Me | iso-Pr | n-Pr | — |
| (315) | tert-Bu | 2-tert-Bu | — | iso-Pr | n-Pr | — |
| (316) | tert-Bu | 2-Me | — | iso-Pr | n-Pr | — |
| (317) | Me | 2-Me | — | iso-Pr | n-Bu | — |
| (318) | Me | 1-Me | 3-Me | iso-Pr | n-Bu | — |
| (319) | tert-Bu | 2-tert-Bu | — | iso-Pr | n-Bu | — |
| (320) | tert-Bu | 2-Me | — | iso-Pr | n-Bu | — |
| (321) | Me | 2-Me | — | iso-Pr | n-Hex | — |
| (322) | Me | 1-Me | 3-Me | iso-Pr | n-Hex | — |
| (323) | tert-Bu | 2-tert-Bu | — | iso-Pr | n-Hex | — |
| (324) | tert-Bu | 2-Me | — | iso-Pr | n-Hex | — |

TABLE 1-continued

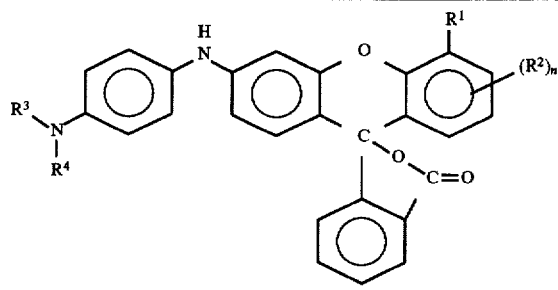

| Compound No. | R¹ | R² (n = 1) | R² (n = 2) | R³ | R⁴ | Melting Point °C. |
|---|---|---|---|---|---|---|
| (325) | Me | 2-Me | — | iso-Pr | n-Oct | — |
| (326) | Me | 1-Me | 3-Me | iso-Pr | n-Oct | — |
| (327) | tert-Bu | 2-tert-Bu | — | iso-Pr | n-Oct | — |
| (328) | tert-Bu | 2-Me | — | iso-Pr | n-Oct | — |

The fluoran compounds of the present invention can be used separately for the preparation of recording materials, each of which giving a specific color depending to the fluoran compound used, however, it is also possible to use them by admixing 2 or more of the fluoran compounds of the present invention or by mixing with other color forming dyestuff. For example, it is possible to prepare a recording material capable of forming real black color by admixing three dyestuff each forming red, blue and green color, respectively, and the other one forming black color.

For the color forming dyestuff which can be admixed with the fluoran compound of the present invention, various color forming dyestuff including fluoran, triphenyl methanephthalide, phenothiazine, spiropyran and rhodaminelactam compounds, can be used.

The fluoran compounds usable for the admixture with the fluoran compound of the present invention are the followings.

3-diethylamino-6-methyl-7-anilinofluoran
3-dibutylamino-6-methyl-7-anilinofluoran
3-(N-ethyl-N-isobutylamino)-6-methyl-7-anilinofluoran
3-(N-methyl-N-propylamino)-6-methyl-7-anilinofluoran
3-(N-ethyl-N-isopentylamino)-6-methyl-7-anilinofluoran
3-diethylamino-7-(o-chloroanilino)fluoran
3-dibutylamino-7-(o-chloroanilino)fluoran
3-(N-ethyl-p-toluidino)-6-methyl-7-anilinofluoran
3-(N-cyclohexyl-N-methylamino)-6-methyl-7-anilinofluoran
3-pyrrolidino-6-methyl-7-anilinofluoran
3-piperidino-6-methyl-7-anilinofluoran
3-dimethylamino-7-(m-trifluoromethylanilino)fluoran
3-dipentylamino-6-methyl-7-anilinofluoran
3-(N-ethoxypropyl-N-ethylamino)-6-methyl-7-anilinofluoran
3-dibutylamino-7-(o-fluoroanilino)fluoran
3-diethylaminobenzo[a]fluoran
3-dimethylamino-6-methyl-7-chlorofluoran
3-diethylamino-5-methyl-7-dibenzylaminofluoran
3-diethylamino-7-dibenzylaminofluoran
3-diehtylamino-5-chlorofluoran
3-diethylamino-6-(N,N'-dibenzylamino)fluoran
3,6-dimethoxyfluoran Also, for examples of the near infrared rays absorbing dyestuff, 3-(4-(4-(4-anilino)-anilino)anilino-6-methyl-7-chlorofluoran, 3,3-bis(2-(4-dimethylaminophenyl)-2-(4-methoxyphenyl)vinyl)-4,5,6,7-tetrachlorophthalide, 3,6,6'-tris(dimethylamino)spiro[fluorene-9,3'-phthalide] and the like, can be given.

The admixing ratio of the fluoran compound to the fluoran compound of the present invention in the admixture described above can be optionally selected in a rate range of from 1:100 to 100:1, however, it is preferable to use said fluoran compound in an amount of from 5 to 30% by weight respective to the amount of the fluoran compound of the present invention.

As the usage of the color forming recording materials comprising the fluoran compound of the present invention, photorecording materials, chelating recording materials, pressure sensitive recording materials, thermal recording materials, etc. are known. However, it is more typical to use such color forming recording materials for recording materials based on the color forming mechanism, wherein a color former reacts with a developer to thereby form color, and for which pressure sensitive copying papers and thermal recording papers are exemplified as the representative. Since some of the fluoran compounds of the present invention can intensively absorb light having a wavelength of near infrared area, it is also possible to use the fluoran compounds of the present invention for a near infrared rays absorbing dyestuff used for recording materials.

The manufacturing of thermal recording papers by using the fluoran compound of the present invention can be attained according to the known manufacturing method for ordinary recording papers using presently-used color forming dyestuff, where, for example, the recording papers can be manufactured by coating suspension, wherein fine granules of a color forming dyestuff compound and the same of a developer are dispersed in aqueous solution of water-soluble binder, onto papers or the like and by subsequently drying the papers. The mixing ratio of the developer to the color forming dyestuff may vary appropriately depending upon the type of such compounds, however, it is normally in a range of from 1 to 10 parts by weight, and preferably from 2 to 5 parts by weight, respective to 1 part by weight of the color forming dyestuff. In the suspension described above, sensitizer, filler, dispersant, color-formed image stabilizer, antioxidant, desensitizer, antitack agent, defoamer, photostabilizing agent, fluorescent brightening agent, etc. can be contained, if appropriate.

Furthermore, over and under the color forming layer, some other layers can be additionally formed, and wherein antioxidant and photostabilizing agent can be contained. Or, such antioxidant and photostabilizing agent, prepared in a form being included in microcapsules, can be contained in the layers, if appropriate.

For examples of the developer to be used in the manufacturing method as described above, bisphenols, such as bisphenol A, 4,4'-sec-butylidenebisphenol, 4,4'-cyclohexylidenebisphenol, 2,2-dimethyl-3,3-bis(4-hydroxyphenyl)butane, 2,2'-dihydroxydiphenyl, pentamethylene-bis(4-hydroxybenzoate), 2,2-dimethyl-3,3-di(4-hydroxyphenyl)pentane and 2,2-di(4-hydroxyphenyl) hexane, sulphur-containing bisphenols, such as 4,4'-dihydroxydiphenyl thioether, 1,7-di(4-hydroxyphenylthio)-3,5-dioxa heptane, 2,2'-bis(4-hydroxyphenylthio)diethyl ether and 4,4'-dihydroxy-3,3'-dimethyldiphenl thioether, 4-hydroxybenzoic acid esters, such as benzyl 4-hydroxybenzoate, ethyl 4-hydroxybenzoate, propyl 4-hydroxybenzoate, isopropyl 4-hydroxybenzoate, butyl 4-hydroxybenzoate, isobutyl 4-hydroxybenzoate, chlorobenzyl 4-hydroxybenzoate, methylbenzyl 4-hydroxybenzoate and diphenylmethyl 4-hydroxybenzoate, metal salts of benzoic acid, such as zinc benzoate and zinc 4-nitrobenzoate, salicylic acids such as 4-2-(4-methoxyphenyloxy)ethyloxy)salicylate, metal salts of salicylic acid such as zinc salicylate, hydroxysulfones, such as 4,4'-dihydroxydiphenylsulfone, 2,4'-dihydroxydiphenylsulfone, 4-hydroxy-4'-methyldiphenylsulfone, 4-hydroxy-4'-isopropoxydiphenylsulfone, 4-hydroxy-4'-butoxydiphenylsulfone, 4,4'-dihydroxy-3,3'-diallyldiphenylsulfone, 3,4-dihydroxy-4'-methyldiphenylsulfone and 4,4'-dihydroxy-3,3',5,5'-tetrabromodiphenylsulfone, 4-hydroxyphthalate diesters, such as dimethyl 4-hydroxyphthalate, dicyclohexyl 4-hydrophthalate and diphenyl 4-hydroxyphthalate, hydroxynaphthoic acid esters such as 2-hydroxy-6-carboxynaphthalene, hydroxyacetophenone, p-phenylphenol, benzyl 4-hydroxyphenylacetate, p-benzylphenol, hydroquinone-monobenzyl ether, trihalomethylsulfones such as tribromomethylphenylsulfone, sulfonylureas such as 4,4'-bis(p-toluenesulfonylaminocarbonylamino)diphenyl methane, charge-transfer complexes such as tetracyanoquino dimethane, etc. can be given.

Similarly, for examples of the sensitizer, higher fatty acid amides such as stearic acid, benzamide, anilide stearate, anilide acetoneelate, thioacetoanilide, dibenzyl oxalate, di(4-methylbenzyl)oxalate, di(4-chlorobenzyl)oxalate, dimethyl phthalate, dimethyl terephthalate, dibenzyl terephthalate, dibenzyl isophthalate, bis(tert-butylphenol) compounds, diethers of 4,4'-dihydroxydiphenylsulfone, 1,2-bis(phenoxy)ethane, 1,2-bis(4-methylphenoxy)ethane, 1,2-bis(3-methylphenoxy)ethane, 2-naphthol benzyl ether, diphenylamine, carbazole, 2,3-di-m-tolyl butane, 4-benzylbiphenyl, 4,4'-dimethylbiphenyl, m-terphenyl, di-β-naphthylphenylenediamine, phenyl 1-hydroxynaphthoate, 2-naphtylbenzyl ether, 4-methylphenylbiphenyl ether, 2,2bis(3,4-dimethylphenyl)ethane, 2,3,5,6-tetramethyl-4'-methyldiphenyl methane, etc. can be given. However, ethers, such as 1,2-bis(3-methylphenoxy)ethane and 2-naphthylbenzyl ether, and aromatic hydrocarbons, such as m-terphenyl and 4-benzylbiphenyl, are preferable for the sensitizer.

For examples of the filler, clay, talc, caoline, satin white, titanium oxide, calcium carbonate, magnesium carbonate, barium sulfate, magnesium silicate, aluminium silicate, etc. can be given.

For examples of the dispersant, sulfosuccinic acid esters such as dioctylsodium sulfosuccinate, sodium dodecylbenzenesulfonate, sodium salts and fatty acid salts of laurylalcohol sulfate, etc. can be given.

For examples of the color-formed image stabilizer, epoxy-containing diphenylsulfones, such as 4-benzyloxy-4'-(2-methylglycidyloxy)-diphenylsulfone and 4,4'-diglycidyloxydiphenylsulfone, 1,4-diglycidyloxybenzene, 4-(α-(hydroxymethyl)benzyloxy)-4'-hydroxydiphenylsulfone, 2-propanol derivatives, salicylic acid derivatives, metal salts of oxynaphthoic acid derivatives (particularly zinc salts), and water-insoluble zinc compounds can be given.

For examples of the antioxidant, 2,2'-methylenebis(4-methyl-6-tert-butylphenol), 2,2'-methylenebis(4-ethyl-6-tert-butylphenol), 4,4'-propylmethylenebis(3-methyl-6-tert-butylphenol), 4,4'-butylidenebis(3-methyl-6-tert-butylphenol), 4,4'-thiobis(2-tert-butyl-5-methylphenol), 1,1,3-tris(2-methyl-4-hydroxy-5-tert-butylphenyl)butane, 1,1,3-tris(2-methyl-4-hydroxy-5-cyclohexylphenyl)butane, etc. can be given.

For examples of the desensitizer, aliphatic higher alcohols, polyethylene glycol, guanidine derivatives, etc. can be given.

For examples of the antitack agent, stearic acid, zinc stearate, calcium stearate, carnauba wax, paraffin wax, wax ester, etc. can be given.

For examples of the photostabilizing agent, ultraviolet rays absorbing agents composed of salicylate compounds, such as phenyl salicylate, p-tert-butylphenyl salicylate and p-octylphenyl salicylate, ultraviolet rays absorbing agents composed of benzophenones, such as 2,4-dihydroxybenzophenone, 2-hydroxy-4-methoxybenzophenone, 2-hydroxy-4-benzyloxybenzophenone, 2-hydroxy-4-octyloxybenzophenone, 2-hydroxy-4-dodecyloxybenzophenone, 2,2'-dihydroxy-4methoxybenzophenone, 2,2'-dihydroxy-4,4'-dimethoxybenzophenone and 2-hydroxy-4-methoxy-5-sulfobenzophenone, ultraviolet rays absorbing agents composed of benzotriazoles, such as 2-(2'-hydroxy-5'-methylphenyl)benzotriazole, 2-(2'-hydroxy-5'-tert-butylphenyl)benzotriazole, 2-(2'-hydroxy-3',5'-di-tertbutylphenyl)benzotriazole, 2-(2'-hydroxy-3'-tert-butyl-5'-methylphenyl)-5chlorobenzotriazole, 2-(2'-hydroxy-3',5'-di-tert-butylphenyl)-5chlorobenzotriazole, 2-(2'-hydroxy-3', 5'-di-tert-amylphenyl)benzotriazole, 2-[2'-hydroxy-3'-(3", 4",5",6",-tetrahydrophthalimidomethyl)-5'-methylphenyl] benzotriazole, 2-(2'-hydroxy-5'-tert-octylphenyl) benzotriazole, 2-[2'-hydroxy-3',5'-bis(α, α-dimethylbenzyl) phenyl]-2H-benzotriazole, 2-(2'-hydroxy-3'-dodecyl-5'-methylphenyl)benzotriazole, 2-(2'-hydroxy-3'-undecyl-5'-methylphenyl) benzotriazole, 2-(2'-hydroxy-3'-undecyl-5'-methylphenyl)benzotriazole, 2-(2'-hydroxy-3'-tridecyl-5'-methylphenyl)benzotriazole, 2-(2'-hydroxy-3'-tetradecyl-5'-methylphenyl)benzotriazole, 2-(2'-hydroxy-3'-pentadecyl-5'-methylphenyl)benzotriazole, 2-(2'-hydroxy-3'-hexadecyl-5'-methylphenyl)benzotriazole, 2-[2'-hydroxy-4'-(2"-ethylhexyl)oxyphenyl]benzotriazole, 2-[2'-hydroxy-4'-(2"-ethylheptyl)oxyphenyl]benzotriazole, 2-[2'-hydroxy-4'-(2"-ethyloctyl)oxyphenyl]benzotriazole, 2-[2'-hydroxy-4'-(2"-propyloctyl)oxyphenyl]benzotriazole, 2-[2'-hydroxy-4'-(2"-propylheptyl)oxyphenyl]benzotriazole, 2-[2'-hydroxy-4'-(2"-propylhexyl)oxyphenyl]benzotriazole, 2-[2'-hydroxy-4'-(1"-ethylhexyl)oxyphenyl]benzotriazole, 2-[2'-hydroxy-4'-(1"-ethylheptyl)oxyphenyl]benzotriazole, 2-[2'-hydroxy-4'-(1'-ethyloctyl)oxyphenyl]benzotriazole, 2-[2'-hydroxy-4'-(1"-propyloctyl)oxyphenyl]benzotriazole, 2-[2'-hydroxy-4'-(1"-propylheptyl)oxyphenyl]benzotriazole, 2-[2'-hydroxy-4'-(1"-propylhexyl)oxyphenyl]benzotriazole, and condensed compounds of polyethylene glycol and methyl-3-[3-tert-butyl-5(2H-benzotriazole-2-yl)-4-hydroxyphenyl] propionate, ultraviolet rays absorbing agents composed of cyanoacrylates, such as 2'-ethylhexyl-2-cyano-3,3-diphenylacrylate and ethyl-2-cyano-3,3-diphenylacrylate, and ultraviolet rays absorbing agents composed of hindered amines, such as bis(2,2,6,6-tetramethyl-4-piperidyl) sebacate, succinic acid-bis(2,2,6,6-tetramethyl-4-piperidyl) ester and 2-(3,5-di-tert-butyl)malonate-bis(1,2,2,6,6-pentamethyl-4-piperidyl) ester, can be given.

Pressure sensitive copying papers using the fluoran compound of the present invention as the color forming dyestuff can be manufactured by a method similar to the one having been employed for the manufacturing of ordinary copying papers using known color forming dyestuff, such as fluoran compounds. According thereto, for example, the pressure sensitive copying papers are produced as the following. Firstly, a sheet coated with a color former is prepared by coating the dispersion of the fluoran compound of the present invention, which is contained in microcapsules in advance, prepared with appropriate dispersant, onto the paper. Also, a sheet coated with developer is prepared by coating the suspension of the developer onto the paper. Then, both of the sheets prepared are combined in an unit to prepare the pressure sensitive paper. When combining the both sheets into an unit, a sheet, in which the microcapsules containing the color former solution in organic solvent are coated and held on the surface of the under side of the said sheet, can be placed to the upper side of the unit paper, while the other sheet, in which the developer (acidic substance) is coated and held on the surface of the upper side of the sheet, can be placed to the under side of the unit paper. Or, it is also possible to prepare the pressure sensitive copying paper in a form, such like self-content papers, wherein the microcapsules and the developer suspension are both coated on the same surface of a sheet. For the developer to be used in this method, any of known products can be used, however, inorganic acidic substance, such as acid clay, activated clay, apatalgite, bentonite, colloidal silica, aluminium silicate, magnesium silicate, zinc silicate, tin silicate, calcined caoline and talc, aliphatic carboxylic acids, such as oxalic acid, maleic acid, tartaric acid, citric acid, succinic acid and stearic acid, aromatic carboxylic acids, such as benzoic acid, p-tert-butylbenzoic acid, phthalic acid, gallic acid, salicylic acid, 3-isopropylsalicylic acid, 3-phenylsalicylic acid, 3-cyclohexylsalicylic acid, 3,5-di-tert-butylsalicylic acid, 3-methyl-5-benzylsalicylic acid, 3-phenyl-5-(2,2-dimethylbenzyl)salicylic acid, 3,5-di-(2-methylbenzyl) salicylic acid and 2-hydroxy-1-benzyl-3-naphthoic acid, and the metal salts, such as zinc, magnesium, aluminium and titanium, of said aromatic carboxylic acids, phenol resin developers, such as p-phenylphenolformalin resin and p-butylphenol-acetylene resin, admixture of said phenol resin developer and any of the metal salt of the aromatic carboxylic acid given above, etc., can be used.

BEST MODE FOR CARRYING OUT THE INVENTION

Now, the present invention is explained in detail with referring to the examples described hereinbelow, however, it should be noted that the present invention shall not be limited to the scope described in the following examples.

EXAMPLE 1
(Example for synthesis of Compound 1)

To 38 g of concentrated sulfuric acid, were added 7.8 g (0.029 mol) of 2-(2-hydroxy-3,5-dimethyl)benzoyl benzoate and 7.7 g (0.032 mol) of 3-methoxy-4'-dimethylaminodiphenylamin then subjecting them to a reaction for 24 hours while stirring at room temperature. After the reaction, the product was dispersed into a solution composed of 140 ml of 20% aqueous solution of sodium hydroxide and 100 ml of toluene, then the dispersion was subjected to reflux for 2 hours under heating while stirring. The water-layer was then removed by separation, and the toluene layer was condensed after washing it by using water. The crystals precipitated were filtered and dried, thereby affording 10 g of pale yellowish white crystals of 2,4-dimethyl-6-(4-dimethylaminophenyl)aminofluoran of which melting point being of from 234.5° to 234.7° C.

[Reference Example 1]
Preparation of the benzoyl benzoate derivative to be used for the Example 1

In 64 ml of dichlorobenzene, were added 7.1 g of phthalic anhydride and 17.4 g of anhydrous aluminium chloride, and 5.3 g of 2,4-dimethylphenol was further added thereto while cooling the reacting solution with ice in order not to elevate the temperature more than room temperature. After stirring the solution for 24 hours at room temperature, the solution was further kept for the reaction for 3 hours at 90° C. to complete it. The reacted product was dispersed into diluted hydrochloric acid solution, then extracted with aqueous alkali solution, and neutralized with diluted hydrochloric acid to precipitate the crystals. The crystals were then filtered and dried, thereby affording 7.0 g of objective white crystals of 2-(2-hydroxy-3,5-dimethyl)benzoyl benzoate of which melting point being of from 172.9° to 173.6° C.

[Reference Example 2]
Preparation of the benzoyl benzoate derivative to be used for the Example 1 (Alternative method)

To 100 ml of tetrachloroethane, were added 7.1 g of phthalic anhydride and 5.6 g of anhydrous zirconium chloride, and subsequently 5.3 g of 2,4-dimethylphenol was added thereto while cooling the reacting solution with ice in order not to elevate the temperature more than room temperature. After following the same procedure as described in the Reference Example 1, 7.3 g of objective white crystals of 2-(2-hydroxy-3,5-dimethyl)benzoyl benzoate, of which melting point being of from 173.1° to 173.9° C., was obtained.

EXAMPLE 2-1
Preparation of the diphenylamine derivative to be used for the Example 1

To 12 g of pseudocumene, were added 12.1 g of resorcine, 10.0 g of N,N-dimethyl-p-phenylenediamine and 0.85 g of 85% phosphoric acid, and were subjected to reflux for 5 hours at a temperature of from 180° to 200° C. while distillating resulting water. The product reacted was dissolved in 300 ml of methylisobutyl ketone and was subsequently extracted with 20% aqueous solution of sodium hydroxide. The alkaline extract was then further extracted into methylisobutyl ketone while neutralizing it with diluted hydrochloric acid. The precipitate resulted by the condensation of the organic layer was filtered and then dried, thereby affording brown powder of which melting point being of from 105.4° to 105.7° C. The yield was 62.9%.

EXAMPLE 2-2
Preparation of the diphenylamine derivative to be used for the Example 1 (Alternative method)

To 60 ml of pseudocumene, were added 43.9 g of acetyl form of anisidine, 63.8 g of N,N-dimethylbromoaniline, 1.0 g of copper(I) iodide and 73.5 g of anhydrous potassium carbonate, and were subjected to reflux for 7 hours at a temperature of from 195° to 205° C. The solution then pored into 200 ml of ethanol, added with 45.0 of potassium hydroxide and reflux for 2 hours to take place the hydrolysis. Then the solution was dispersed into 2000 ml of water and neutralized with diluted hydrochloric acid to result in the precipitate. 59 g of the crude crystals obtained were further subjected to recrystallization by using methanol, thereby affording 50.2 g of white crystals of which melting point being of from 115.5° to 117.5° C. The yield was 78.0%.

EXAMPLE 2-3
Preparation of the diphenylamine derivative to be used for the Example 1 (Alternative method)

To a 500 ml volume flask for reaction, were placed 115 g of N-acetylanisidine, 149 g of p-N,N-dimethylaminobromoaniline, 193 g of anhydrous potassium carbonate, 3.9 g of bis(1,10-phenanthroline)copper(II) nitrate monohydrate and 115 ml of 1,2,4-trimethylbenzene, and were subjected to a reaction under ordinary pressure and stirring for 5 hours at a temperature of from 190° to 200° C.

Water resulted in during the reaction was azeotropically distilled together with 1,2,4-trimethylbenzene, and the later was recovered into the reaction cycle after separating it from water.

To the reacted solution being cooled down to 70° C., were added 400 ml of ethyl alcohol and 115 g of 85% potassium hydroxide, and were further subjected to reflux for 2 hours.

After cooling down the reacted solution to 90° C., 400 ml of water and 800 ml of toluene were added thereto, and subsequently the solution was stirred for 30 min. at 60° C.

The resulting organic layer was separated and then washed three times with each 200 ml of water, then solvent contained in the organic layer was distilled under reduced pressure.

The residue obtained was subjected to recrystallization by using 400 ml of methanol, thereby affording 119.0 g of objective compound, 4-N,N-dimethylamino-3'-methoxydiphenylamine.

The melting point of the compound was in a range of from 115.0° to 117.0° C.

EXAMPLE 3
(Example for synthesis of Compound 4)

To 50 g of concentrated sulfuric acid, were added 11.0 g (0.039 mol) of 2-(2-hydroxy-3,4,6-trimethyl)benzoyl benzoate and 7.7 g (0.032 mol) of 3-methoxy4'-dimethylaminophenylamine, and were subjected to a reaction for 3 days while stirring at room temperature. After following the same procedure as described in the Reference Example 1, 9.7 g of pale yellowish white crystals of 1,3,4-trimethyl-6-(4-dimethylaminophenyl)aminofluoran, of which melting point being of from 244.2° to 245.5° C., was obtained.

EXAMPLE 4
(Preparation of thermal recording papers)
Color forming dyestuff dispersion (A dispersion)

| | |
|---|---|
| Compound according to the invention (Compound 1 in the Example 1) | 7.0 g |
| 15% aqueous solution of polyvinyl alcohol | 30.0 g |
| Filler (calcium carbonate) | 13.5 g |
| Pure water | 49.5 g |
| Developer dispersion (B dispersion) | |
| 4-isopropoxy-4'-hydroxydiphenylsulfone | 7.0 g |
| 15% aqueous solution of polyvinyl alcohol | 30.0 g |
| Filler (calcium carbonate) | 13.5 g |
| Pure water | 49.5 g |
| Filler dispersion (C dispersion) | |
| 15% aqueous solution of polyvinyl alcohol | 30.0 g |
| Filler (calcium carbonate) | 20.5 g |
| Pure water | 49.5 g |

Each of the mixtures composed as described above were subjected to grinding in a sand grinder, respectively, to prepare dispersions, A, B and C. Then, 1 part by weight of A dispersion, 2 parts by weight of B dispersion and 1 part by weight of C dispersion were admixed to prepare a coating solution. The coating solution was coated to white papers by using a wire rod (No. 12), then the said coated papers were dried and subjected to calendering to prepare the thermal recording papers.

EXAMPLE 5

Following the same procedure as described in the Example 4, except replacing the compound of the invention in the A dispersion of the Example 4 from the Compound 1, [2,4-dimethyl-6-(4-dimethylaminophenyl)aminofluoran], to the Compound 4 synthesized in the Example 3, [1,3,4-trimethyl-6-(4-dimethylaminophenyl)aminofluoran], thermal recording papers were prepared.

EXAMPLE 6

Following the same procedure as described in the Example 4, except replacing the developer in the B dispersion of the Example 4 from 4-isopropoxy-4'-hydroxydiphenylsulfone to 4,4'-dihydroxy-3,3'-diallyldiphenylsulfone, thermal recording papers were prepared.

EXAMPLE 7

Following the same procedure as described in the Example 4, except replacing the composition of the C dispersion of the Example 4 to the following composition;

| | |
|---|---|
| m-terphenyl | 7.0 g |
| 15% aqueous solution of polyvinyl alcohol | 30.0 g |
| Filler (calcium carbonate) | 13.5 g |
| Pure water | 49.5 g | thermal recording papers were prepared.

Comparative Example 1

Thermal recording papers were prepared according to the same procedure as described in the Example 4, except substituting the compound of the invention in the color forming dyestuff dispersion described above to 2-anilino-3-methyl-6-dibutylaminofluoran.

Comparative Example 2

Thermal recording papers were prepared according to the same procedure as described in the Example 4, except substituting the compound of the invention in the color forming dyestuff dispersion described above to 2,3-dimethyl-6-(4-dimethylaminophenyl)aminofluoran.

Test Example 1
(Test on photostability of thermal recording papers)

Each of the thermal recording papers prepared in the Examples 4 and 6 and the Comparative Examples, respectively, were subjected to both-paper-sides heating at 170° C. by using a dry heater (manufactured by Kishino Scientific Machinery) to form color thereon. Subsequently, photostability tests during 12, 24 and 48 hours were respectively carried out on both color-formed parts and color-unformed parts of the papers by using a photostability testing apparatus (Ultraviolet rays long-life fade meter, Type: FAL-5, Manufactured by Suga Experimental Machinery). The density of the color-formed images on the papers before and after the test was determined by using a Macbeth reflection densitometer and a filter BW (Ratten 9106). For the measurement on the color-unformed parts, a filter Y (Ratten #106) was also used, since the color-unformed parts became yellowish. The results are presented in Table 2.

TABLE 2

(Photostability Test)

| Condition Examples | Color-unformed Parts (Background) | | | Color-formed Parts | | | |
|---|---|---|---|---|---|---|---|
| | Pre- | 12 hr | 24 hr | Pre- | 12 hr | 24 hr | 48 hr |
| Example 4 (Compound 1) | 0.05 Y0.07 | 0.06 Y0.10 | 0.08 Y0.12 | 1.01 | 0.65 (64%) | 0.44 (44%) | 0.25 (25%) |
| Example 6 (Compound 1) | 0.09 Y0.09 | 0.09 Y0.11 | 0.09 Y0.12 | 1.31 | 1.23 (94%) | 0.99 (76%) | |
| Comparision 1 | 0.07 Y0.09 | 0.08 Y0.17 | 0.07 Y0.12 | 1.34 | 0.65 (49%) | 0.31 (23%) | 0.10 (7%) |

In the results for the color-formed parts in the Table 2 shown above, the percentage in each parenthesis denotes the value obtained by dividing the value measured after the testing with the value measured before the testing, namely the image-remaining ratio, wherein the greater values acquiring less discoloration of the images. Whereas, the greater values given by Macbeth reflection densitometer denote higher density of the color-formed images.

As shown in the Table 2, it was demonstrated in the photostability test described above that the thermal recording papers prepared according to the present invention can provide better whiteness of the background of the papers and less discoloration of the color-formed images on the papers.

Test Example 2

The amount of the color forming dyestuff remaining in each of the recording papers prepared according to the Examples, 4, 5, 6 and 7, and the Comparative examples, 1 and 2, after having the photostability test during 24 hours was respectively determined by using liquid chromatography. The results are shown in Table 3.

TABLE 3

(Remaining Ratio of Color forming Dyestuff After Photostability Test)

| Condition | Remaining Ratio of Dyestuff | |
|---|---|---|
| Examples | Color-unformed Parts | Color-formed Parts |
| Example 4 (Compound 1) | 94% | 75% |
| Example 5 (Compound 4) | 48% | 57% |
| Example 6 (Compound 1) | 97% | 47% |
| Example 7 (Compound 1) | 98% | 48% |
| Comparative Example 1 | 13% | 15% |
| Comparative Example 2 | 29% | 52% |

The remaining ratio of the color forming dyestuff after the photostability test demonstrates that the compound provided with the greater remaining ratio acquired less decomposition of the fluoran compound due to light and that the color-unformed parts still have kept their capability to form color even after having the photostability test.

Test Example 3

Now, the results obtained in the Test Example 2 are presented with actual images. Namely, background part of the recording papers prepared according to each of the Examples, 4 and 6, and the Comparative Example 1 before and after the photostability test was color-formed, respectively, and the density of the color-formed images were then measured by using Macbeth reflection densitometer. The results are shown in Table 4 shown below.

TABLE 4

(Color Formation Test on Background of Recording paper after having 24 Hours Photostability Test)

| | Items | | |
|---|---|---|---|
| Examples | Color-formed Density Before Exposure | Color-formed Density After Exposure | Rate of Color Formation |
| Example 4 (Compound 1) | 1.09 | 1.02 | 94% |
| Example 6 (Compound 1) | 1.36 | 1.25 | 92% |
| Comparative Example 1 | 1.27 | 0.68 | 54% |

$$\text{Color Formation Rate} = \frac{\text{Macbeth's Value for Color-formed Image After Exposure}}{\text{Macbeth's Value for Color-formed Image Before Exposure}} \times 100$$

Utilization for Industries

According to the present invention, fluoran compounds having excellent photostability and being resistant to the decomposition due to light can be provided, and recording materials having excellent properties in whiteness of the background of the recording material under light and in photostability of the color-formed images on the recording materials to light as well as in sufficient color forming capability of color-unformed part of the materials even after having exposed them to light, can also be provided.

What is claimed is:

1. Fluoran compounds represented by the following general formula (I);

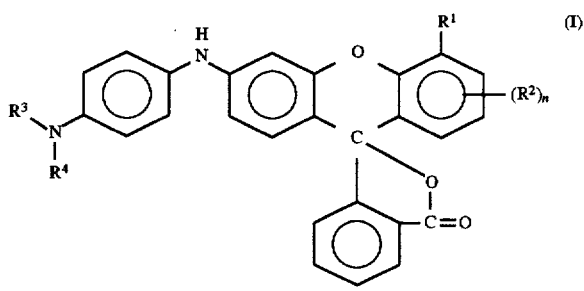

wherein $R^1$ is alkyl containing 1 to 4 carbon atoms, $R^3$ is alkyl containing 1 to 8 carbon atoms, $R^4$ is hydrogen or alkyl containing 1 to 8 carbon atoms, or $R^3$ and $R^4$ may bond with each other to form a ring together with a N atom, $R^2$ is alkyl containing 1 to 4 carbon atoms, and n denotes 0, 1 or 2, however, the substituents represented by $R^2$ may be different with each other when n is 2.

2. Fluoran compounds represented by the following general formula (I');

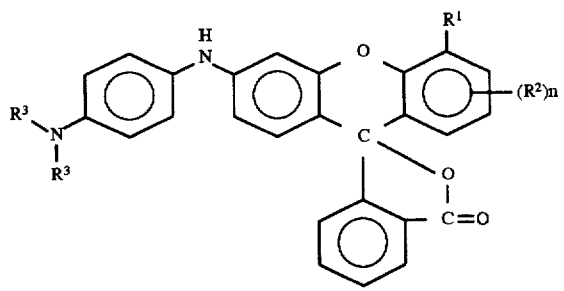

wherein $R^1$ is alkyl containing 1 to 4 carbon atoms, $R^3$ is alkyl containing 1 to 8 carbon atoms, $R^2$ is alkyl containing 1 to 4 carbon atoms, and n denotes 1 or 2, however, the substituents represented by $R^2$ may be different with each other when n is 2.

3. Color forming recording materials comprising the fluoran compound represented by the general formula (I) according to the claim 1.

4. Color forming recording materials comprising the fluoran compound represented by the general formula (I') according to the claim 2.

* * * * *